United States Patent
Greenlee et al.

(10) Patent No.: US 9,096,582 B2
(45) Date of Patent: Aug. 4, 2015

(54) GAMMA SECRETASE MODULATORS

(71) Applicants: William Greenlee, Teaneck, NJ (US); Dmitri Pissarnitski, Scotch Plains, NJ (US); Zhiqiang Zhao, Scotch Plains, NJ (US); Zhaoning Zhu, Warfield (GB)

(72) Inventors: William Greenlee, Teaneck, NJ (US); Dmitri Pissarnitski, Scotch Plains, NJ (US); Zhiqiang Zhao, Scotch Plains, NJ (US); Zhaoning Zhu, Warfield (GB)

(73) Assignee: MERCK SHARP & DOHME CORP, Rahway, NJ (US)

( * ) Notice: Subject to any disclaimer, the term of this patent is extended or adjusted under 35 U.S.C. 154(b) by 0 days.

(21) Appl. No.: 14/354,992

(22) PCT Filed: Oct. 26, 2012

(86) PCT No.: PCT/US2012/062041
§ 371 (c)(1),
(2) Date: Apr. 29, 2014

(87) PCT Pub. No.: WO2013/066740
PCT Pub. Date: May 10, 2013

(65) Prior Publication Data
US 2014/0296311 A1 Oct. 2, 2014

Related U.S. Application Data

(60) Provisional application No. 61/553,384, filed on Oct. 31, 2011.

(51) Int. Cl.
*C07D 413/10* (2006.01)

(52) U.S. Cl.
CPC .................................. *C07D 413/10* (2013.01)

(58) Field of Classification Search
None
See application file for complete search history.

(56) References Cited

U.S. PATENT DOCUMENTS

| 8,450,343 B2 * | 5/2013 | Huang et al. .................. 514/303 |
| 2011/0015190 A1 | 1/2011 | Huang et al. |

* cited by examiner

*Primary Examiner* — Kamal Saeed
(74) *Attorney, Agent, or Firm* — J. Eric Thies; John C. Todaro

(57) ABSTRACT

Disclosed herein are compounds of Formula (I) and pharmaceutically acceptable salts thereof, wherein each of the substituents is given the definition as set forth in the specification and claims. Also disclosed are pharmaceutical compositions containing compounds of Formula (I) and use of the compounds in the treatment of neurodegenerative diseases or conditions such as Alzheimer's disease.

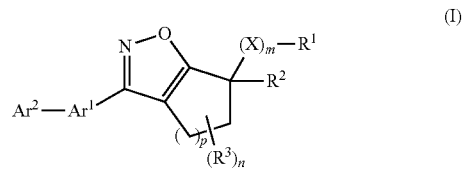

18 Claims, No Drawings

GAMMA SECRETASE MODULATORS

CROSS REFERENCE TO RELATED APPLICATIONS

This application is a U.S. National Phase application under 35 U.S.C. §371 of PCT Application No. PCT/US2012/062041, filed Oct. 26, 2012, which claims priority under 35 U.S.C. §119(e) from U.S. Ser. No. 61/553,384 filed Oct. 31, 2011.

BACKGROUND

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Amyloid beta peptides (Aβs), which are metabolites of amyloid precursor protein (hereinafter referred to as APP), are considered to be greatly involved in degeneration and loss of neurons as well as onset of demential conditions (for example, see Klein W L, et al *Proceeding National Academy of Science USA*, Sep. 2, 2003, 100(18), p. 10417-22), suggest a molecular basis for reversible memory loss.

Nitsch R M, and 16 others, *Antibodies against β-amyloid slow cognitive decline in Alzheimer's disease*, Neuron, May 22, 2003, 38(4), p. 547-554) suggest that the main components of Aβ are Aβ40 consisting of 40 amino acids and Aβ42 having two additional amino acids at the C-terminal. The Aβ40 and Aβ42 tend to aggregate (for example, see Jarrell J T et al, The carboxy terminus of the β amyloid protein is critical for the seeding of amyloid formation: implications for the pathogenesis of Alzheimer's disease, Biochemistry, May 11, 1993, 32(18), p. 4693-4697) and constitute the main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer's disease and Down syndrome*, Proceeding National Academy of Science USA, June 1985, 82(12), p. 4245-4249.).

Furthermore, it is known that mutations of APP and presenelin genes, which are observed in familial Alzheimer's disease, increase production of Aβ40 and Aβ42 (for example, see Gouras G K, et al, Intraneuronal Aβ142 accumulation in human brain, American Journal of Pathology, January 2000, 156(1), p. 15-20. Also, see Scheuner D, et al, Nature Medicine, August 1996, 2(8), p. 864-870; and Forman M S, et al, Differential effects of the Swedish mutant amyloid precursor protein on β-amyloid accumulation and secretion in neurons and nonneuronal cells, Journal of Biological Chemistry, Dec. 19, 1997, 272(51), p. 32247-32253.). Therefore, compounds which reduce production of Aβ40 and Aβ42 are expected to be agents for controlling progress of Alzheimer's disease or for preventing the disease.

These Aβs are produced when APP is cleaved by β-secretase and subsequently cleaved by gamma (γ)-secretase. In consideration of this, creation of inhibitors of γ-secretase and β-secretase has been attempted for the purpose of reducing production of Aβs. Many of these known secretase inhibitors are peptides or peptidomimetics such as L-685,458. L-685,458, an aspartyl protease transition state mimic, is a potent inhibitor of γ-secretase activity (Biochemistry, Aug. 1, 2000, 39(30), p. 8698-8704).

There is a need for new compounds, formulations, treatments and therapies to treat diseases and disorders associated with production of Aβs. It is, therefore, an object of this invention to provide compounds which may be useful in the treatment or prevention or amelioration of such diseases and disorders.

SUMMARY OF THE INVENTION

In its many embodiments, the present invention provides a novel class of compounds as gamma secretase modulators (including inhibitors, antagonists and the like), pharmaceutical compositions comprising one or more such compounds, and methods of treatment, prevention, inhibition or amelioration of one or more diseases associated with production of Aβs using such compounds or pharmaceutical compositions.

Compounds of this invention termed gamma secretase modulators have the structure of Formula (I)

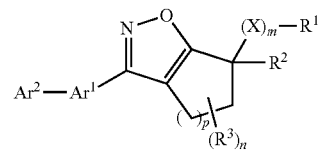

or a pharmaceutically acceptable salt thereof, wherein $R^1$ is 1) hydrogen, 2) (C1-C6)alkyl optionally substituted with 1 to 5 halogens or phenyl, wherein the phenyl is optionally substituted with 1 to 3 halogens, 3) phenyl optionally substituted with 1 to 3 (C1-C6)alkyls or 1 to 5 halogens, or 4) (C4-C6)cycloalkyl optionally substituted with 1 to 3 (C1-C6)alkyls or 1 to 5 halogens;

$R^2$ is 1) hydrogen, 2) (C1-C6)alkyl optionally substituted with 1 to 5 halogens or phenyl, wherein the phenyl is optionally substituted with 1 to 3 halogens, or 3) phenyl optionally substituted with 1 to 3 halogens;

$R^3$ is (C1-C6)alkyl, —OH or halogen;

X is —$NR^4$—, —O—, —S—, or —$SO_2$—;

$R^4$ is hydrogen or (C1-C3)alkyl;

p is 1 to 3;

m is 0 or 1;

n is 0 to 3; and $Ar^2$—$Ar^1$ is selected from the group consisting of

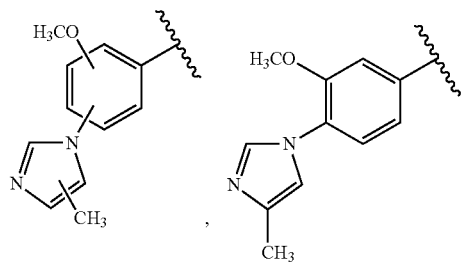

In an embodiment, the present invention provides for pharmaceutical compositions comprising at least one compound of Formula (I). In another embodiment, the present invention provides for methods for treating a neurodegenerative disease or condition amenable to treatment by modulation of gamma secretase, e.g., Alzheimer's disease.

DETAILED DESCRIPTION OF THE INVENTION

As used above, and throughout this disclosure, the following terms, unless otherwise indicated, shall be understood to have the following meanings:

"At least one" means there is at least one, and examples include 1, 2 or 3, or 1 or 2, or 1.

"One or more" means the same as "at least one."

"Patient" and "subject" means an animal, such as a mammal, e.g., a human being, and is preferably a human being.

"Alkyl" means an aliphatic hydrocarbon group, which may be straight or branched and comprising about 1 to about 12 carbon atoms in the chain. More preferred alkyl groups contain about 1 to about 6 carbon atoms in the chain or about 1 to about 2 or 3 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. Non-limiting examples of suitable alkyl groups include methyl, ethyl, n-propyl, isopropyl and t-butyl.

"Cycloalkyl" means a non-aromatic monocyclic ring system comprising about 3 to about 6 carbon atoms, preferably about 4 to about 6 carbon atoms. The cycloalkyl can be optionally substituted as defined herein. Non-limiting examples of suitable saturated monocyclic cycloalkyls include cyclopropyl, cyclobutyl, cyclopentyl and cyclohexyl.

"Halogen" means fluorine, chlorine, bromine, or iodine. Fluorine, chlorine and bromine are preferred. A substituent which is a halogen atom means —F, —Cl, —Br, or —I, and "halo" means fluoro, chloro, bromo or iodo substituents bonded to the moiety defined, e.g., "haloalkyl" means an alkyl, as defined above, wherein one or more of the bonding positions on the alkyl moiety typically occupied by hydrogen atoms are instead occupied by a halo group.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties. For example, a phenyl optionally substituted with an indicated group of substituents includes unsubstituted phenyl as well as phenyl substituted with any of the indicated substituents.

It should also be noted that any carbon atom as well as any heteroatom with unsatisfied valences in the text, schemes, examples, Tables, etc. herein is assumed to have the sufficient number of hydrogen atom(s) to satisfy the valences.

The term "effective amount" or "therapeutically effective amount" is meant to describe an amount of compound or a composition of the present invention effective in inhibiting the production and/or deposition of amyloid protein, and thus producing the desired therapeutic, ameliorative, inhibitory or preventative effect.

This invention provides compounds that are modulators (e.g., inhibitors, antagonists and the like) of gamma-secretase (also termed "γ-secretase") and have the Formula (I)

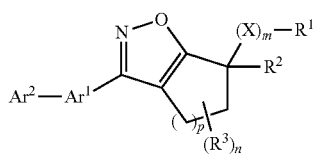

or a pharmaceutically acceptable salt thereof,
wherein
$R^1$ is 1) hydrogen, 2) (C1-C6)alkyl optionally substituted with 1 to 5 halogens or phenyl, wherein the phenyl is optionally substituted with 1 to 3 halogens, 3) phenyl optionally substituted with 1 to 3 (C1-C6)alkyls or 1 to 5 halogens, or 4) (C4-C6)cycloalkyl optionally substituted with 1 to 3 (C1-C6)alkyls or 1 to 5 halogens;
$R^2$ is 1) hydrogen, 2) (C1-C6)alkyl optionally substituted with 1 to 5 halogens or phenyl, wherein the phenyl is optionally substituted with 1 to 3 halogens, or 3) phenyl optionally substituted with 1 to 3 halogens;
$R^3$ is (C1-C6)alkyl, —OH or halogen;
X is —NR$^4$—, —O—, —S—, or —SO$_2$—;
$R^4$ is hydrogen or (C1-C3)alkyl;

p is 1 to 3;
m is 0 or 1;
n is 0 to 3; and
Ar²—Ar¹ is selected from the group consisting of

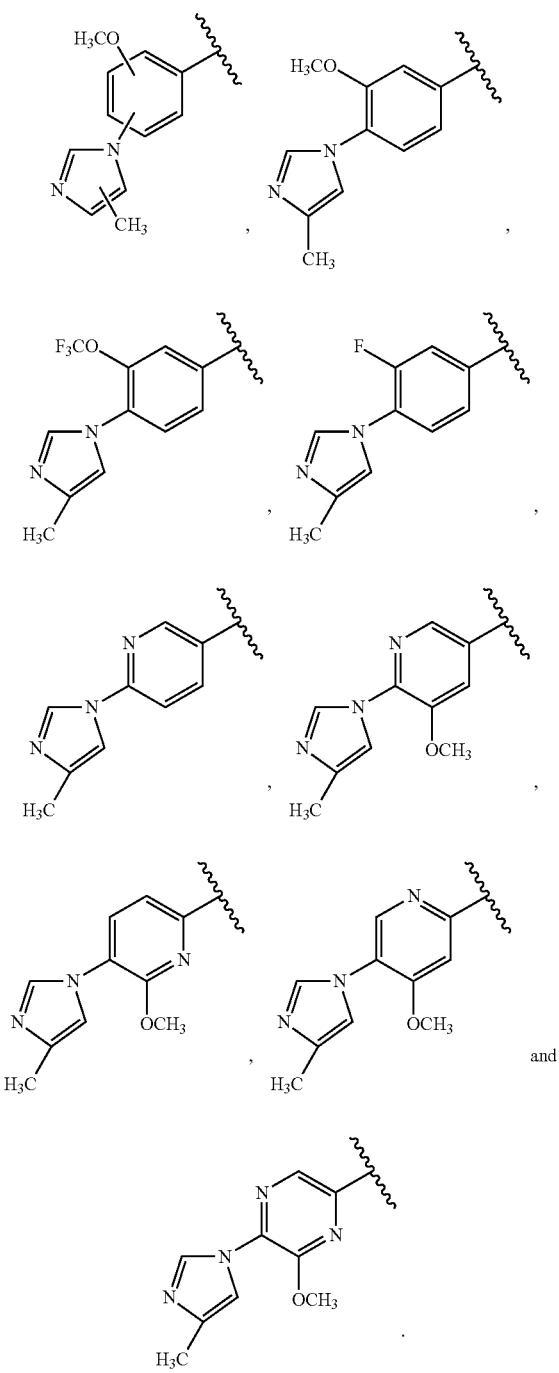

The compounds of the invention have been found to be modulators (inhibitors, antagonists, and the like) of gamma-secretase activity and are believed to be Useful in providing treatment of conditions or disease states which can be treated by modulation of gamma-secretase activity, for example, Alzheimer's disease, Down Syndrome, mild cognitive impairment, glaucoma, cerebral amyloid angiopathy, stroke, dementia, microgliosis, brain inflammation, traumatic brain injury and olfactory function loss.

In one embodiment of the compounds of Formula (I), Ar²—Ar¹ is

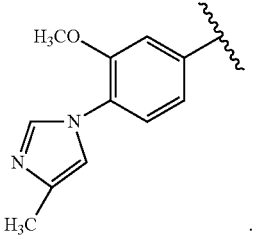

In another embodiment of the compounds of Formula (I), p is 2 and n is 0.

In another embodiment of the compounds of Formula (I), the halogen is fluoro.

In another embodiment of the compounds of Formula (I), X is —NR⁴—, m is 1, n is 0, and R¹ is (C1-C6)alkyl optionally substituted with 1 to 5 halogens or phenyl, wherein the phenyl is optionally substituted with 1 to 3 halogens.

In another embodiment of the compounds of Formula (I), when X is m is 1, and n is 0, R¹ is (C1-C6)alkyl substituted with phenyl, wherein the phenyl is substituted with 1 to 3 halogens or 1 or 2 halogens.

In another embodiment of the compounds of Formula (I), when X is —NR⁴—, m is 1, n is 0, R¹ is (C1-C6)alkyl substituted with phenyl, and phenyl is substituted with 1 or 2 halogens, the halogen is fluoro.

In another embodiment of the compounds of Formula (I), X is —NR⁴—, m is 1, n is 0, and R¹ is phenyl optionally substituted with 1 to 3 (C1-C6)alkyls or 1 to 5 halogens, or 1 or 2 halogens, e.g., fluoro.

In another embodiment of the compounds of Formula (I), when X is —NR⁴—, m is 1, n is 0, R¹ is phenyl substituted with 1 or 2 halogens, e.g., fluoro.

In another embodiment of the compounds of Formula (I), when X is —O—, m is 1, and n is 0, R¹ is 1) (C1-C6)alkyl optionally substituted with 1 to 5 halogens or phenyl, wherein the phenyl is optionally substituted with 1 to 3 halogens, or 2) phenyl optionally substituted with 1 to 3 (C1-C6)alkyls or 1 to 5 halogens. In another embodiment, when X is —O—, m is 1, and n is 0, R¹ is 1) (C1-C6)alkyl substituted with phenyl, wherein the phenyl is substituted with 1 or 2 halogens or 2) phenyl substituted with 1 or 2 halogens.

In another embodiment of the compounds of Formula (I), X is —O—, m is 1, n is 0, R¹ is H and R² is phenyl optionally substituted with 1 to 3 halogens, and in particular, 1 or 2 halogens.

In another embodiment of the compounds of Formula (I), X is —O—, m is 1, n is 0, R¹ is H, R² is (C1-C6)alkyl substituted with phenyl, wherein the phenyl is optionally substituted with 1 to 3 halogens, or 1 or 2 halogens.

In another embodiment of the compounds of Formula (I), X is —NR⁴—, m is 1, n is 0, and R¹ is (C4-C6)cycloalkyl optionally substituted with 1 to 3 (C1-C6)alkyls or 1 to 5 halogens.

In another embodiment, the compounds of Formula (I) are selected from the group consisting of

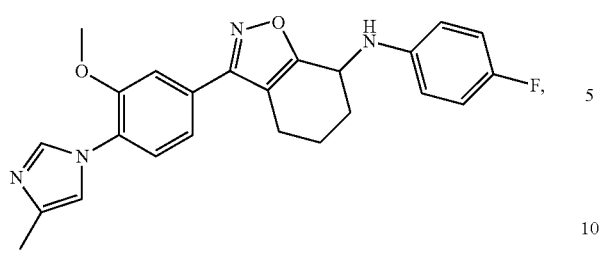
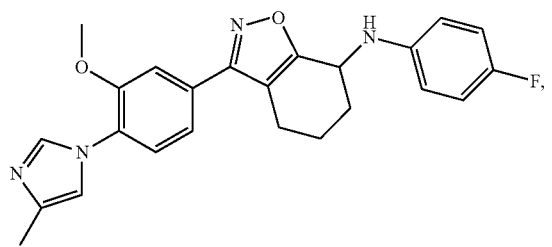
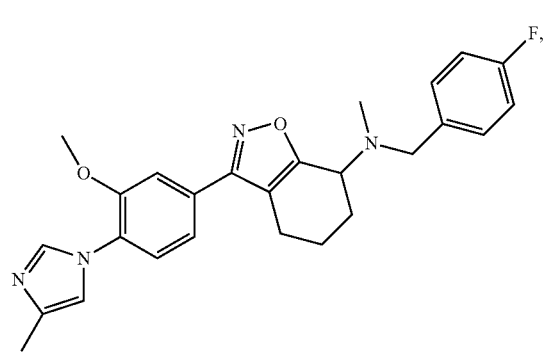
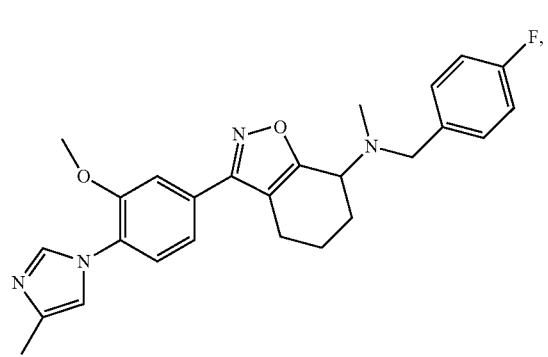
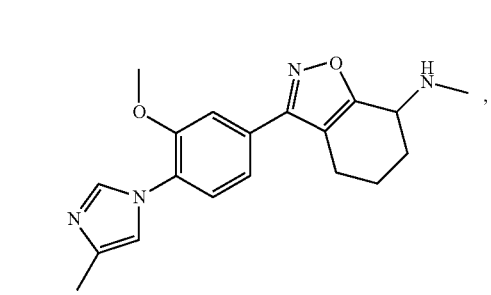
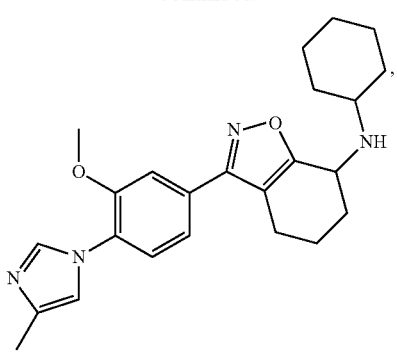
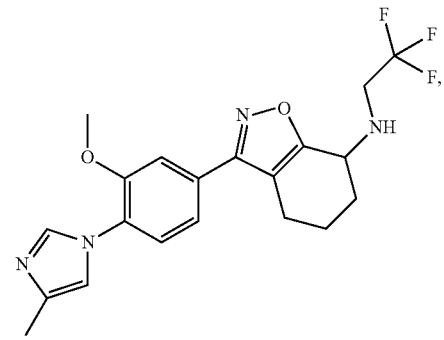
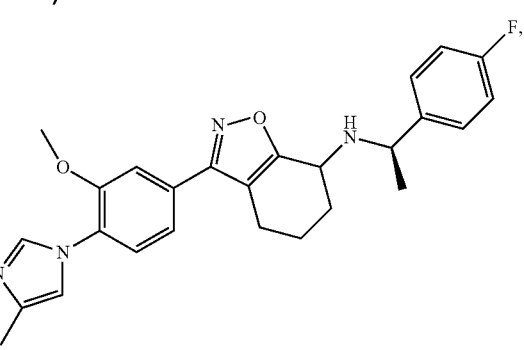
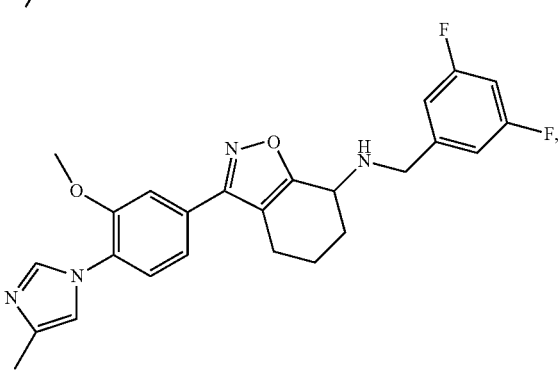
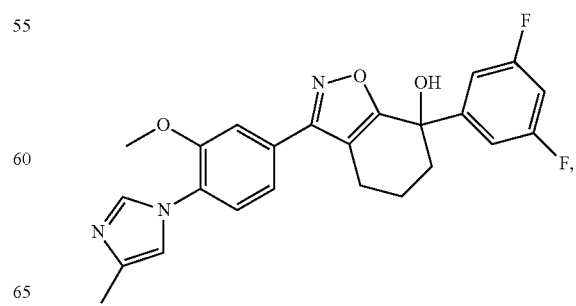

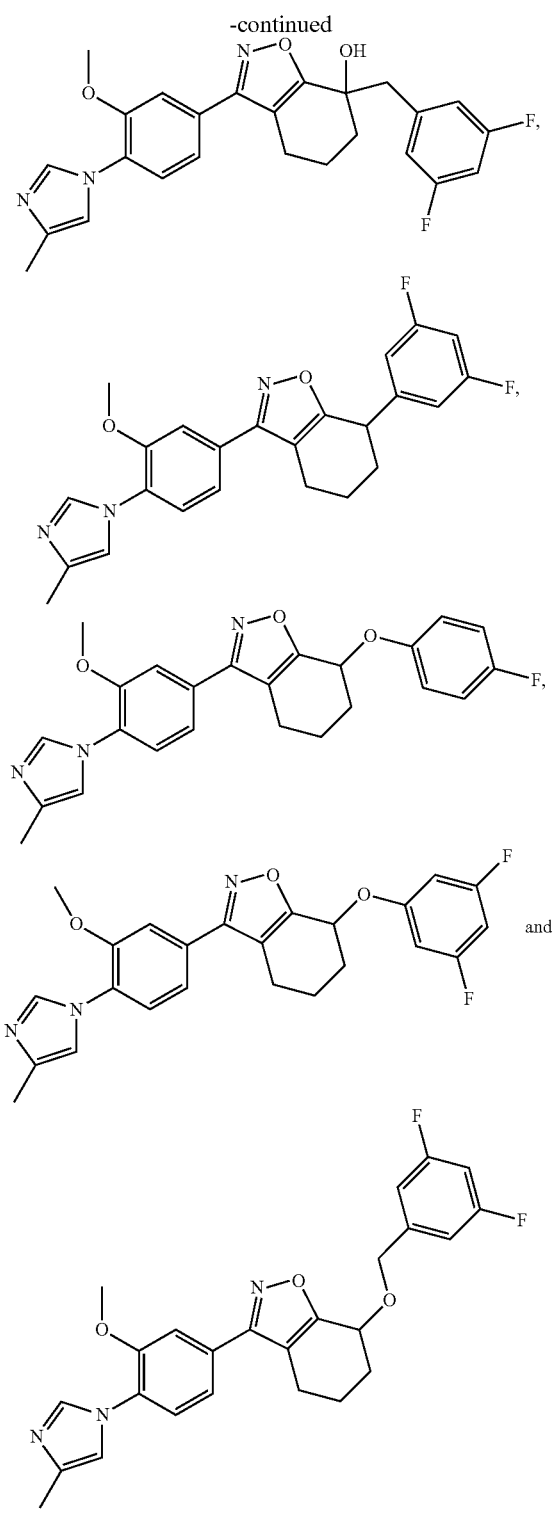

or a pharmaceutically acceptable salt thereof.

The compounds of Formula (I) can form salts, which are also within the scope of this invention. Reference to a compound of Formula (I) herein is understood to include reference to salts thereof, unless otherwise indicated. The term "salt(s)", as employed herein, denotes acidic salts formed with inorganic and/or organic acids. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

All such salts are intended to be pharmaceutically acceptable salts within the scope of the invention and salts are considered equivalent to the free forms of the corresponding compounds for purposes of the invention.

Prodrugs and solvates of the compounds of the invention are also contemplated herein. The term "prodrug", as employed herein, denotes a compound that is a drug precursor that, upon administration to a subject, undergoes chemical conversion by metabolic or chemical processes to yield a compound of Formula (I) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule(s) is/are $H_2O$.

Compounds of Formula (I), and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Polymorphic forms of the compounds of Formula (I), and of the salts, solvates and prodrugs of the compounds of Formula (I), are intended to be included in the present invention.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled compounds of Formula I (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detection. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of Formula (I) can generally be prepared by following procedures analogous to those disclosed in the Schemes and/or in the Examples herein below, by substituting an appropriate isotopically labeled reagent for a non-isotopically labeled reagent.

Representative compounds of the invention include but are not limited to the compounds and Examples described herein.

The compounds of Formula (I) can be useful as gamma secretase modulators and may be useful in the treatment and prevention of diseases such as, for example, central nervous system disorders (such as Alzheimer's disease and Down Syndrome), mild cognitive impairment, glaucoma, cerebral amyloid angiopathy, stroke, dementia, microgliosis, brain inflammation, and olfactory function loss.

Pharmaceutical compositions can comprise at least one compound of Formula (I) or a pharmaceutically acceptable salt thereof and at least one pharmaceutically acceptable carrier. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., herein incorporated by reference in its entirety.

Liquid form preparations include solutions, suspensions and emulsions. Water or water-propylene glycol solutions for parenteral injection or addition of sweeteners and opacifiers for oral solutions, suspensions and emulsions are examples. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The quantity of active compound in a unit dose of preparation may be varied or adjusted from about 1 mg to about 100 mg, preferably from about 1 mg to about 50 mg, more preferably from about 1 mg to about 25 mg, according to the particular application. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, in one to four divided doses.

As indicated above, the compounds of the invention may be useful in the treatment of Alzheimer's disease. Accordingly, in another embodiment of this invention a method of treating Alzheimer's disease is provided comprising administering to a patient in need thereof a therapeutically effective amount of at least one compound of Formula (I) or a pharmaceutically acceptable salt thereof.

In another embodiment of the method of treating Alzheimer's disease, the method comprises administering to a patient in need thereof a therapeutically effective amount of at least one compound of Formula (I) or a pharmaceutically acceptable salt thereof, and a therapeutically effective amount of at least one drug selected from the group consisting of BACE inhibitors; muscarinic antagonists; cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; GABAA inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitor; anti-Abeta vaccine; APP ligands; agents that upregulate insulin cholesterol lowering agents; cholesterol absorption inhibitors; fibrates; LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux.

In another embodiment, a method of treating Alzheimer's disease is provided comprising administering an effective (i.e., therapeutically effective) amount of at least one compound of Formula (I) or a pharmaceutically acceptable salt thereof, in combination with a therapeutically effective amount of at least one cholinesterase inhibitor (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept brand of donepezil hydrochloride), to a patient in need of treatment.

The invention also provides for a method of inhibiting the deposition of amyloid beta protein in, on or around neurological tissue is provided, the method comprising administering to a patient in need thereof a therapeutically effective amount of at least one compound of the Formula (I) or a pharmaceutically acceptable salt thereof.

The invention also provides for a method of modulating (including inhibiting, antagonizing and the like) gamma secretase comprising administering to a patient in need thereof a therapeutically effective amount of at least one compound of the Formula (I) or a pharmaceutically acceptable salt thereof.

The compounds of Formula (I) are also useful in treating a neurodegenerative disease or condition selected from the group consisting of Down's Syndrome, mild cognitive impairment, glaucoma, cerebral amyloid angiopathy, stroke, dementia, microgliosis, brain inflammation, traumatic brain injury and olfactory function loss. The method of treatment comprises administering to a patient in need thereof a therapeutically effective amount of at least one compound of the Formula (I) or a pharmaceutically acceptable salt thereof.

EXAMPLES

The invention disclosed herein is exemplified by the following preparations and examples, which should not be construed to limit the scope of the disclosure.

The following solvents, reagents, and conditions may be referred to by their abbreviations in parenthesis:
Acetic Acid (HOAc)
Acetic anhydride ($Ac_2O$)
Ammonium Acetate ($NH_4Ac$)
Deuterochloroform ($CDCl_3$)
Cesium Carbonate ($Cs_2CO_3$)
Chloroacetone ($ClCH_2C(O)CH_3$)
Diethylazodicarboxylate (DEAD)
Dimethyl formamide (DMF)
Dichloromethane (DCM)
Ethanol (EtOH)
Formic Acid (HCOOH)
Hydroxyl Amine ($NH_2OH$)
Hydrochloric Acid (HCl)
Magnesium Sulfate ($MgSO_4$)
Methanol ($CH_3OH$)
Methyl Cyanide ($CH_3CN$)
Methyl Iodide ($CH_3I$)
N-Chlorosuccinimide (NCS)
Chiralcel® OD column (manufactured by Chiral Technologies, Inc.) (OD Column)
Triphenylphosphine ($Ph_3P$)
Potassium Carbonate ($K_2CO_3$)
Potassium Iodide (KI)
Room Temperature (RT)
Sodium Borohydride ($NaBH_4$)
Sodium Hydride (NaH)
Stannous Chloride ($SnCl_2$)
Tetrahydrofuran (THF)
Trifluoroacetic acid (TFA)
Thin Layer Chromatography (TLC)
Titanium(IV) isopropoxide ($Ti(OPr-i)_4$
Trimethylsilyl chloride (TMSCl)

Experimental Methods

Unless otherwise noted, reagents and solvents were used as received by commercial suppliers.

Preparation 1

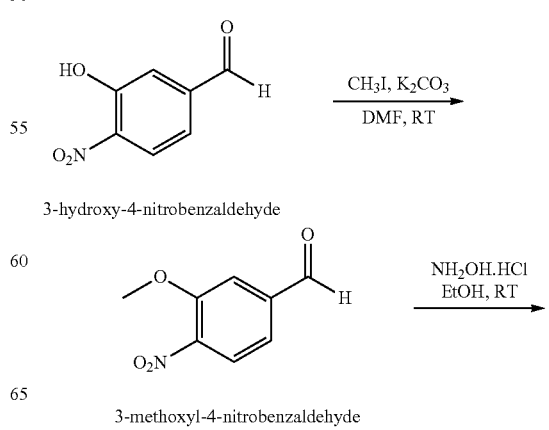

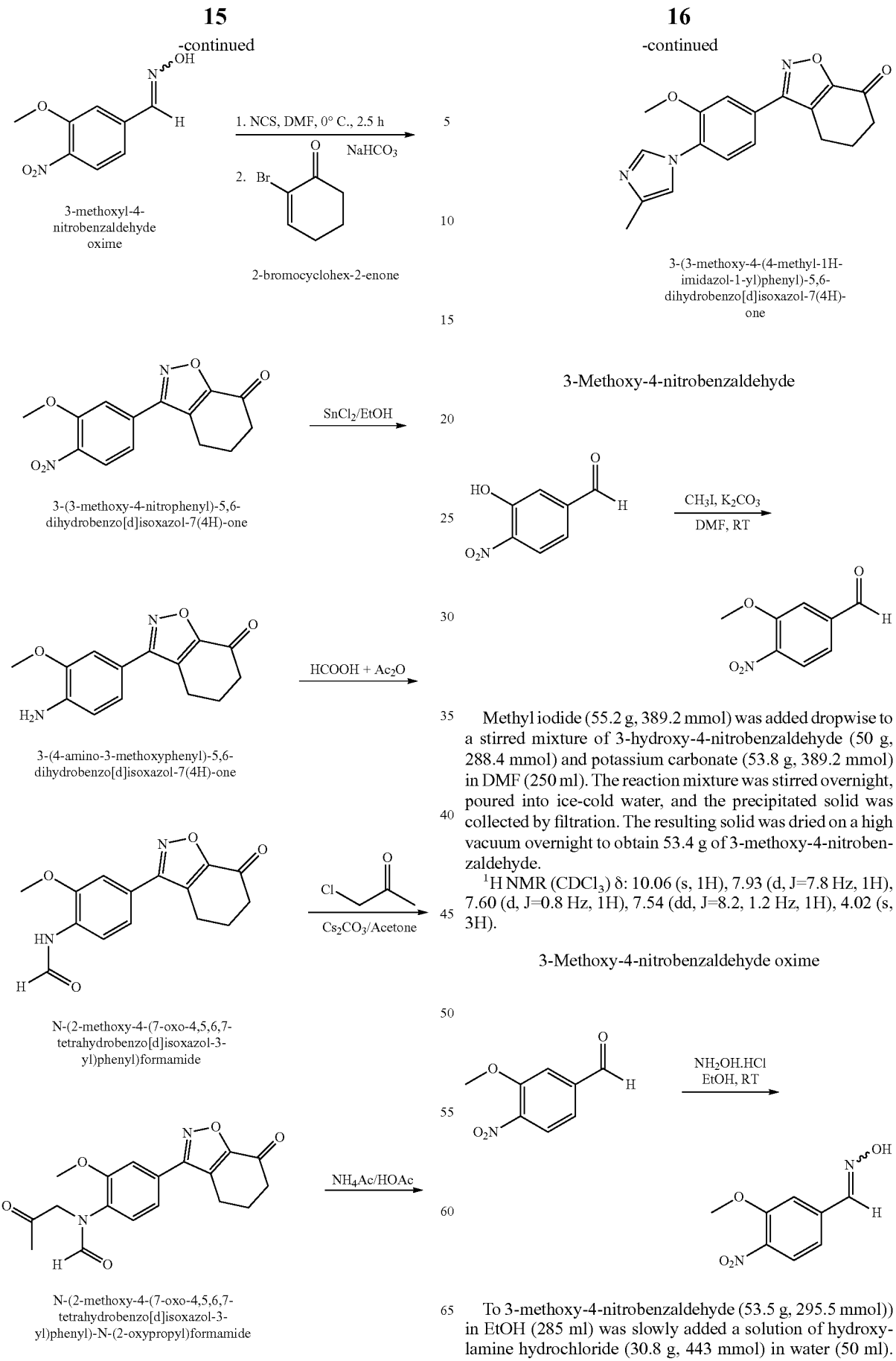

3-Methoxy-4-nitrobenzaldehyde

Methyl iodide (55.2 g, 389.2 mmol) was added dropwise to a stirred mixture of 3-hydroxy-4-nitrobenzaldehyde (50 g, 288.4 mmol) and potassium carbonate (53.8 g, 389.2 mmol) in DMF (250 ml). The reaction mixture was stirred overnight, poured into ice-cold water, and the precipitated solid was collected by filtration. The resulting solid was dried on a high vacuum overnight to obtain 53.4 g of 3-methoxy-4-nitrobenzaldehyde.

$^1$H NMR (CDCl$_3$) δ: 10.06 (s, 1H), 7.93 (d, J=7.8 Hz, 1H), 7.60 (d, J=0.8 Hz, 1H), 7.54 (dd, J=8.2, 1.2 Hz, 1H), 4.02 (s, 3H).

3-Methoxy-4-nitrobenzaldehyde oxime

To 3-methoxy-4-nitrobenzaldehyde (53.5 g, 295.5 mmol)) in EtOH (285 ml) was slowly added a solution of hydroxylamine hydrochloride (30.8 g, 443 mmol) in water (50 ml).

The reaction mixture was stirred overnight, poured into ice-cold water, and the formed precipitate was collected by filtration to furnish 44 g of 3-methoxy-4-nitrobenzaldehyde oxime. The filtrate was extracted with DCM, and the organic phase was washed with water and brine, dried over sodium sulfate, and concentrated to furnish additional 8.2 g of the title product. $^1$H NMR (CDCl$_3$) δ: 8.13 (s, 1H), 7.87 (d, J=8.2 Hz, 1H), 7.51 (s, 1H), 7.35 (s, 1H), 7.18 (dd, J=8.4, 1.4 Hz, 1H), 4.01 (s, 3H).

3-(3-Methoxy-4-nitrophenyl)-5,6-dihydrobenzo[d]isoxazol-7(4H)-one

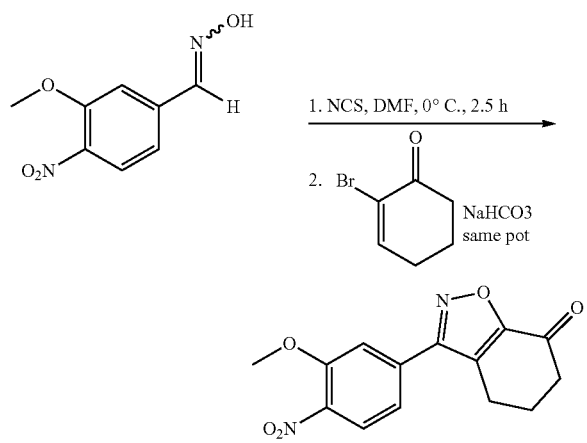

To 3-methoxy-4-nitrobenzaldehyde oxime (5.0 g, 25.5 mmol) in DMF (60 ml) at 0° C. was added N-chlorosuccinimide (4.088 g, 30.61 mmol). The reaction mixture was stirred for 15 min at 0° C., and 1.5 hr at ambient temperature. To the reaction flask was added as solids 2-bromocyclohex-2-enone (6.66 g, 38.2 mmol, prepared as in Kowalski, C. J.; Weber, A. E.; Fields, K. W. J. Org. Chem. (1982), 47(26), 5088-93) followed by sodium bicarbonate (4.29 g, 51 mmol), and the mixture was stirred overnight. The reaction mixture was partitioned between water and dichloromethane, the organic phase was washed with water, sat. NaHCO$_3$, and brine. The organic phase was dried over sodium sulfate and concentrated. The residue was chromatographed on silica gel using hexanes/ethyl acetate mixture as eluent to furnish 4.95 g of the title product. $^1$H NMR (CDCl$_3$) δ: 7.97 (d, J=8.6 Hz, 1H), 7.60 (s, 1H), 7.32 (dd, J=8.4, 1.4 Hz, 1H), 4.05 (s, 3H), 2.99 (t, J=6.1 Hz, 2H), 2.75 (t, J=6.3 Hz, 2H), 2.31 (quin, J=6.3 Hz, 2H).

3-(4-Amino-3-methoxyphenyl)-5,6-dihydrobenzo[d]isoxazol-7(4H)-one

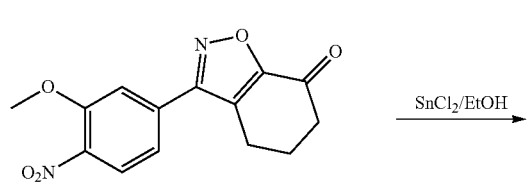

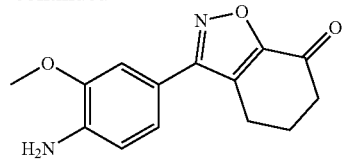

Procedure: To the 3-(3-methoxy-4-nitrophenyl)-5,6-dihydrobenzo[d]isoxazol-7(4H)-one (2.56 g, 8.88 mmol) in dry EtOH (30 ml) was added SnCl$_2$ (8.43 g, 44.4 mmol). The reaction was stirred at 55° C. for 2 hr, cooled to room temperature, diluted with DCM, and NaOH (1M, 100 ml) was added. The mixture was stirred for 30 min and the precipitate was removed by filtration. The filtrate was worked up extractively with DCM and water, and the organic phase was washed with water and brine. After drying over sodium sulfate and concentration, 2.5 g of the title product was obtained, MS(M+H)$^+$=259.

N-(2-Methoxy-4-(7-oxo-4,5,6,7-tetrahydrobenzo[d]isoxazol-3-yl)phenyl)formamide

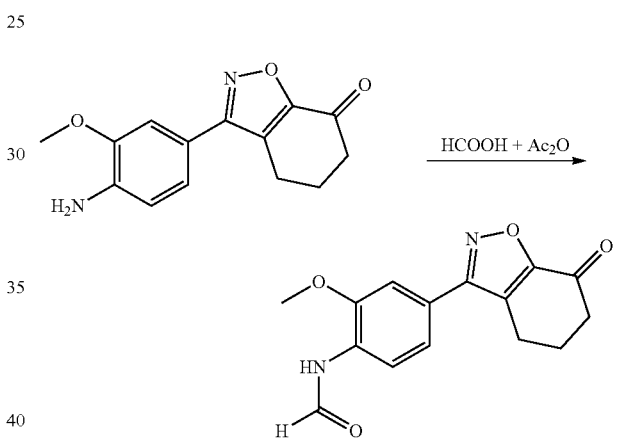

To formic acid (6.24 g, 135.6 mmol) was added dropwise 3.96 g (38.8 mmol) of acetic anhydride (exothermic, cooling with tap water was used). The reaction mixture was stirred for 1 hr. The resulting mixture was transferred via cannula into another reaction flask containing a solution of 3-(4-amino-3-methoxyphenyl)-5,6-dihydrobenzo[d]isoxazol-7(4H)-one in 50 ml of THF (Cooling with tap water was used). The mixture was stirred for 2 hr, extracted with DCM, washed with water and brine, dried over sodium sulfate and concentrated to furnish 2.65 g of the title compound, MS(M+H)$^+$=287.

N-(2-Methoxy-4-(7-oxo-4,5,6,7-tetrahydrobenzo[d]isoxazol-3-yl)phenyl)-N-(2-oxopropyl)formamide

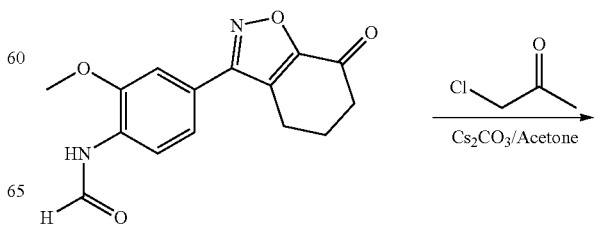

-continued

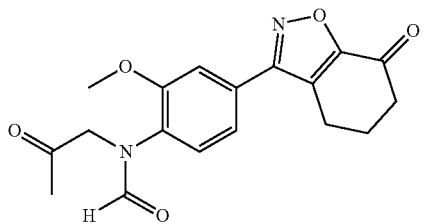

To a mixture of N-(2-methoxy-4-(7-oxo-4,5,6,7-tetrahydrobenzo[d]isoxazol-3-yl)phenyl)formamide (2.66 g, 9.28 mmol), Cs$_2$CO$_3$ (5.37 g, 27.9 mmol), and KI (308 mg, 1.86 mmol) in dry DMF (40 ml) was added chloroacetone (7.72 g, 18.57 mmol) dropwise. The reaction was stirred at 55° C. overnight. Reaction mixture was worked up with water and DCM, organic phase was washed with water and brine, dried over sodium sulfate and concentrated. The product was purified by chromatography on silica gel using a mixture of ethyl acetate and hexanes as the eluent to furnish 1.05 g of the title compound, MS(M+H)$^+$=343.

3-(3-Methoxy-4-(4-methyl-1H-imidazol-1-yl)phenyl)-5,6-dihydrobenzo[d]isoxazol-7(4H)-one

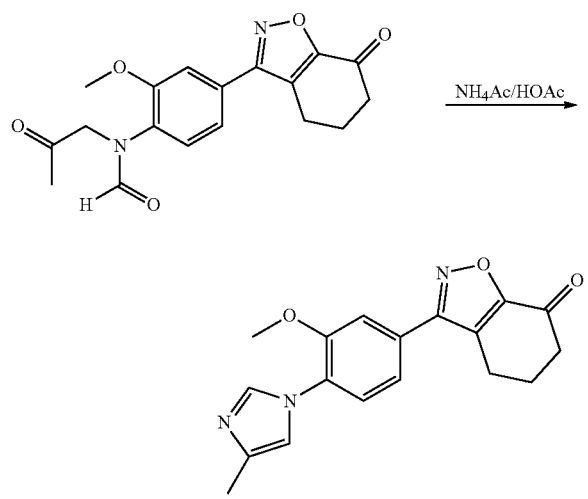

To a mixture of 3-(3-methoxy-4-(4-methyl-1H-imidazol-1-yl)phenyl)-5,6-dihydrobenzo[d]isoxazol-7(4H)-one (1.05 g, 3.069 mmol) and acetic acid (15 ml) was added ammonium acetate. The reaction mixture was stirred under nitrogen at 95° C. overnight. The reaction mixture was cooled and poured into ice water, neutralized with ammonia, extracted with DCM. The organic phase was washed with water and brine, dried over sodium sulfate and concentrated. The product was purified by chromatography on silica gel using a gradient of methanol in DCM (0-5%) as the eluent to furnish 529 mg of the title compound. $^1$H NMR (CDCl$_3$) δ: 7.82 (s, 1H), 7.56 (d, J=1.6 Hz, 1H), 7.40 (d, J=8.2 Hz, 1H), 7.32 (dd, J=8.2, 2.0 Hz, 1H), 6.99 (s, 1H), 3.96 (s, 3H), 3.01 (t, J=6.1 Hz, 2H), 2.75 (t, J=5.9 Hz, 2H), 2.32 (s, 3H), 2.30-2.37 (m, 2H).

Preparation 2

3-(3-methoxy-4-(4-methyl-1H-imidazol-1-yl)phenyl)-4,5,6,7-tetrahydrobenzo[d]isoxazol-7-ol

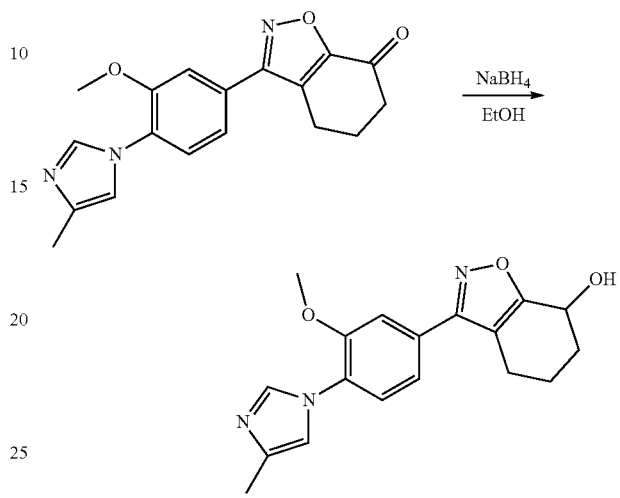

To the 3-(3-methoxy-4-(4-methyl-1H-imidazol-1-yl)phenyl)-5,6-dihydrobenzo[d]isoxazol-7(4H)-one (7.16 mg, 2.22 mmol) in THF/EtOH (v/v=1:1, 26 ml) at ° C., was added NaBH$_4$ (101 mg, 1.66 mmol). The reaction mixture was stirred for 30 min before careful addition of water and extraction with ethyl acetate. The organic phase was washed with water and brine, dried over MgSO4 and concentrated to afford the title product which was used without further purification. $^1$H NMR (CDCl$_3$) δ: 7.74 (s, 1H), 7.51 (s, 1H), 7.29-7.37 (m, 2H), 6.96 (s, 1H), 4.98 (br. s., 1H), 3.92 (s, 3H), 2.70-2.79 (m, 1H), 2.57-2.68 (m, 1H), 2.55 (br. s., 1H), 2.27-2.34 (m, 3H), 1.98-2.11 (m, 3H), 1.86-1.93 (m, 1H), 1.59 (s, 1H).

Method 1

N-(4-Fluorophenyl)-3-(3-methoxy-4-(4-methyl-1H-imidazol-1-yl)phenyl)-4,5,6,7-tetrahydrobenzo[d]isoxazol-7-amine

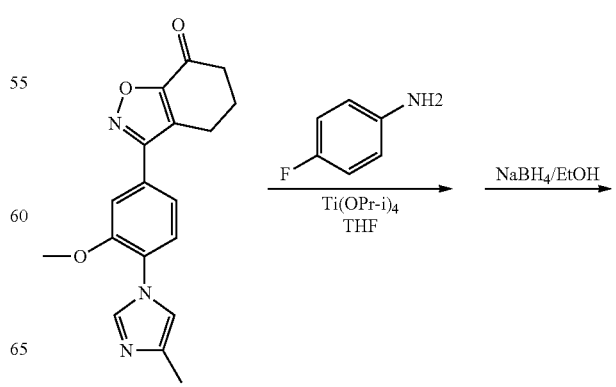

-continued

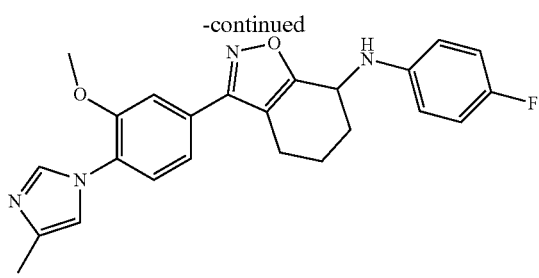

To a mixture of 3-(3-methoxy-4-(4-methyl-1H-imidazol-1-yl)phenyl)-5,6-dihydrobenzo[d]isoxazol-7(4H)-one (850 mg, 2.6 mmol) and 4-fluoroaniline (877 mg, 7.89 mmol) in THF (10 mL) was added Ti(OPr-i)$_4$ (823 mg, 2.9 mmol) and the reaction mixture was stirred at 60° C. overnight. The mixture was cooled to 0° C., and 10.0 mL of dry ethanol was added, followed by NaBH$_4$ (149 mg, 3.4 mmol). The mixture was stirred for 1 hr, precipitate was removed by filtration and washed with ethyl acetate. The filtrate was partitioned between water and ethyl acetate. The aqueous phase was extracted with ethyl acetate. The combined organic phase was washed with brine, dried over MgSO$_4$ and concentrated. The crude product was purified by silica gel chromatography using a gradient of 0-7% of MeOH in DCM to afford the 660 mg of the title product.

$^1$H NMR (CDCl$_3$) δ: 7.75 (s, 1H), 7.52 (s, 1H), 7.30-7.37 (m, 2H), 6.97 (s, 1H), 6.94 (d, J=8.6 Hz, 1H), 6.72 (dd, J=9.0, 4.3 Hz, 1H), 4.63-4.76 (m, 1H), 3.92 (s, 3H), 3.83 (d, J=12.9 Hz, 3H), 2.62-2.82 (m, 2H), 2.34 (s, 3H), 2.11-2.25 (m, 1H), 1.88-2.06 (m, 3H). MS(M+H)$^+$=419.

The product was further resolved by chiral OD column using a mixture of 2-propanol and hexanes as solvent to afford two enantiomers.

Method 2

7-(3,5-Difluorophenyl)-3-(3-methoxy-4-(4-methyl-1H-imidazol-1-yl)phenyl)-4,5,6,7-tetrahydrobenzo[d]isoxazol-7-ol

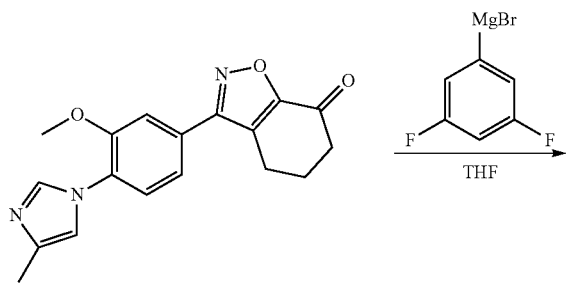

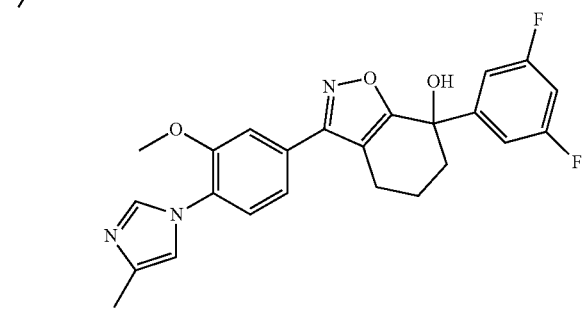

To a mixture of 3-(3-methoxy-4-(4-methyl-1H-imidazol-1-yl)phenyl)-5,6-dihydrobenzo[d]isoxazol-7(4H)-one (880 mg, 2.72 mmol) in THF (15 ml) at 0° C., was added slowly (3,5-difluorophenyl)magnesium bromide (6.54 mL of 0.5 M solution in THF, 3.27 mmol) and the reaction was stirred for 3 hr. Additional amount of (3,5-difluorophenyl)magnesium bromide (6.0 mL of 0.5 M solution in THF, 3.0 mmol) was added and stirring was continued at 0° C. for 2 hr. The reaction mixture was quenched with water, extracted with ethyl acetate, and the organic phase was washed with water and brine, dried over sodium sulfate and concentrated. The crude product was purified by silica gel chromatography using 0-6% MeOH in DCM as solvent to afford the 828 mg of the title product.

$^1$H NMR (CDCl$_3$) δ: 7.75 (s, 1H), 7.51-7.57 (m, 1H), 7.33-7.41 (m, 2H), 6.96-7.01 (m, 1H), 6.91 (d, J=6.3 Hz, 2H), 6.73-6.82 (m, 1H), 3.94 (s, 3H), 3.05 (s, 1H), 2.75-2.86 (m, 2H), 2.31 (s, 3H), 2.23-2.29 (m, 1H), 2.03-2.15 (m, 2H), 1.85-1.97 (m, 1H) MS(M+H)$^+$=438.

Method 3

7-(3,5-Difluorophenyl)-3-(3-methoxy-4-(4-methyl-1H-imidazol-1-yl)phenyl)-4,5,6,7-tetrahydrobenzo[d]isoxazole

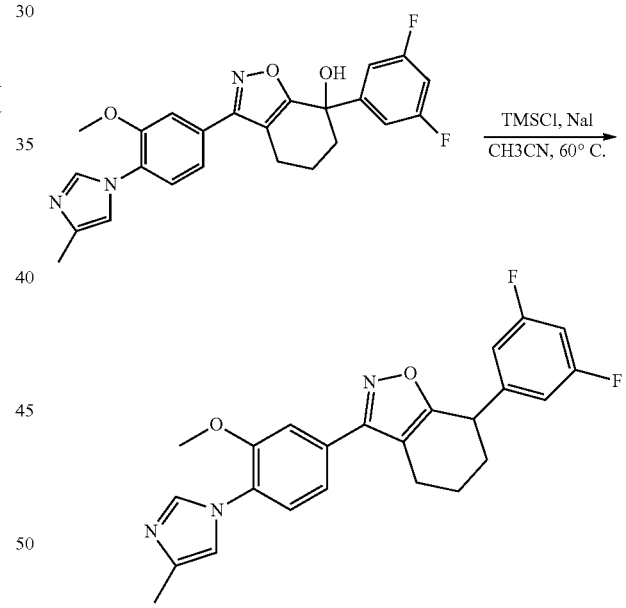

To a suspension of NaI (1.54 g, 10.3 mmol) in CH$_3$CN (20 mL) was added TMSCl (1.12 g, 10.27 mmol) and a solution of 7-(3,5-difluorophenyl)-3-(3-methoxy-4-(4-methyl-1H-imidazol-1-yl)phenyl)-4,5,6,7-tetrahydrobenzo[d]isoxazol-7-ol (691 mg, 1.6 mmol) in CH$_3$CN (1.0 mL) The reaction mixture was stirred at 60° C. overnight, cooled, and partitioned between water and DCM. The organic phase was washed with 10% aq. Na$_2$S$_2$O$_3$, water, and brine, dried over MgSO$_4$ and concentrated. The crude product was purified by silica gel chromatography using 0-5% MeOH in DCM as solvent to afford 445 mg of the title product.

$^1$H NMR (CDCl$_3$) δ: 7.78 (s, 1H), 7.56 (s, 1H), 7.38 (s, 2H), 6.98 (s, 1H), 6.64-6.78 (m, 2H), 4.20 (t, J=5.9 Hz, 1H), 3.96

(s, 3H), 2.69-2.84 (m, 2H), 2.32 (s, 3H), 2.25-2.30 (m, 1H), 1.89-2.01 (m, 2H), 1.78-1.88 (m, 1H). MS(M+H)⁺=422.

Method 4

7-(4-Fluorophenoxy)-3-(3-methoxy-4-(4-methyl-1H-imidazol-1-yl)phenyl)-4,5,6,7-tetrahydrobenzo[d]isoxazole

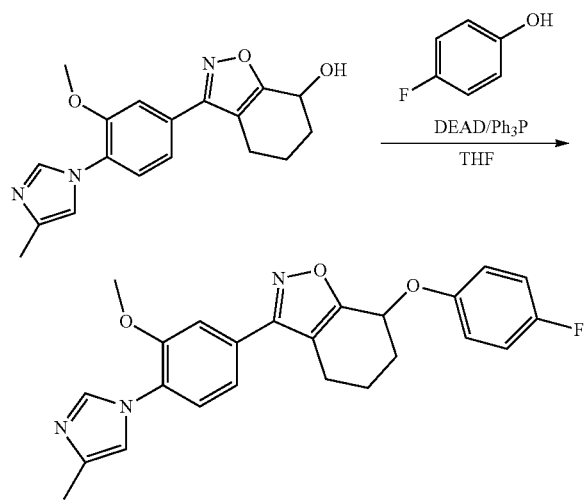

To a mixture of 3-(3-methoxy-4-(4-methyl-1H-imidazol-1-yl)phenyl)-4,5,6,7-tetrahydrobenzo[d]isoxazol-7-ol (48 mg, 0.149 mmol) in THF (1.0 mL) was added 4-flurophenol (23 mg, 0.2 mmol), Ph₃P (58 mg, 0.22 mmol) and DEAD (39 mg, 0.22 mmol). The reaction mixture was stirred over night at 50° C. The reaction mixture cooled, diluted with EtOAc, washed with water and brine, dried over MgSO₄ and concentrated. The crude product was purified by preparative TLC using 5% MeOH in DCM as solvent to afford 27 mg of the title product.

¹H NMR (CDCl₃) δ: 7.75 (s, 1H), 7.63-7.72 (m, 1H), 7.50-7.58 (m, 1H), 7.43-7.49 (m, 1H), 7.30-7.38 (m, 2H), 6.99-7.10 (m, 3H), 6.97 (s, 1H), 5.34 (t, J=3.7 Hz, 1H), 3.92 (s, 3H), 2.78-2.87 (m, 1H), 2.61-2.72 (m, 1H), 2.33-2.37 (m, 1H), 2.30 (s, 3H), 1.91-2.15 (m, 3H). MS(MH⁺)=420.

Method 5

7-(3,5-Difluorobenzyloxy)-3-(3-methoxy-4-(4-methyl-1H-imidazol-1-yl)phenyl)-4,5,6,7-tetrahydrobenzo[d]isoxazole

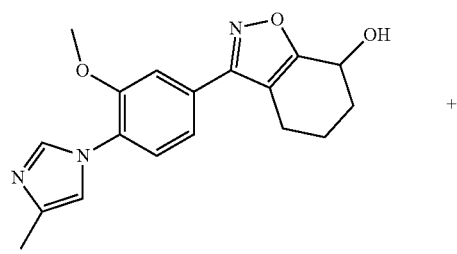

To the 3-(3-methoxy-4-(4-methyl-1H-imidazol-1-yl)phenyl)-4,5,6,7-tetrahydrobenzo[d]isoxazol-7-ol (48 mg, 0.15 mmol) in DMF (2 ml) at 0° C., was added NaH (7 mg, 0.18 mmol). The mixture was stirred for 10 min before addition of 1-(bromomethyl)-3,5-difluorobenzene. Stirring was continued for 1 hr before addition of water (3 mL) and extraction with ethyl acetate. The organic phase was washed with water, brine, dried over MgSO₄ and concentrated. The crude product was purified by preparative TLC using 5% of MeOH in DCM as solvent to afford the title product. ¹H NMR (CDCl₃) δ: 7.82 (br. s., 1H), 7.53 (s, 1H), 7.30-7.40 (m, 214), 6.89-7.03 (m, 2H), 6.73 (t, J=9.0 Hz, 1H), 4.84 (d, J=12.9 Hz, 1H), 4.76 (d, J=13.7 Hz, 1H), 4.64 (t, J 3.7 Hz, 1H), 3.93 (s, 3H), 2.73-2.82 (m, 1H), 2.57-2.68 (m, 1H), 2.33 (br. s., 314), 2.17-2.26 (m, 1H), 1.87-2.07 (m, 3H). MS(M+H)⁺=452.

Assays:

Cell Based γ-Secretase Assay (In Vitro Assay Method)

Human embryonic kidney (HEK) 293 cells stably transfected with APPsw-lon in pcDNA3.1 vector (Invitrogen) were treated with gamma secretase modulator (GSM) compounds (see Table below) for 5 hrs. Aβ in conditioned media was measured using MesoScale Discovery (MSD) technology based sandwich immunoassays. Aβ42 was measured using a pair of labeled antibodies TAG-G2-11 (described in Ida, N. et al., Journal of Biological Chemistry, 1996, 271, p. 22908-22914) and biotin-4G8 (Covance); γ-secretase activity is expressed as the concentration of compound producing 50% inhibition of the enzyme activity. The data presented below in the Table were the means of two independent experiments. As shown below in the Table, the compounds of the invention had an Aβ42 IC50 in the range of 39 nM to 12,177 nM.

Cerebrospinal Fluid (CSF) Aβ Analysis (In Vivo Assay Method)

Male CD rats (100 g; Charles River Laboratories) were orally administered a GSM compound (formulated in 20% hydroxypropyl β-cyclodextin; 5 ml/kg). Three hours later, the animals were euthanized with excess CO₂, and CSF was immediately collected from the cisterna magna and frozen on dry ice; only clear samples were analyzed. Rat CSF Aβ42 was analyzed using AlphaLISA Amyloid Assay kits (Perkin-Elmer) according to the manufacturer's instructions. In vivo activity of the tested GSM compounds is expressed as the percentage of Aβ42 reduction in CSF after administration of the compound and is presented in the Table.

TABLE

| Structure | Comments | MS(M + H)+ | Method | Aβ42 IC50, nM | % CSF Aβ42 Reduction After 30 mg/kg Dosing |
|---|---|---|---|---|---|
| 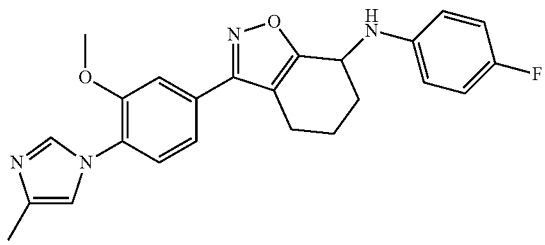 [SMILES: COc1cc(-c2noc3c2CCCC3Nc2ccc(F)cc2)ccc1-n1cnc(C)c1] | enantiomer 1 detailed procedure given | 419 | Method 1 | 39.4 | 58 |
| 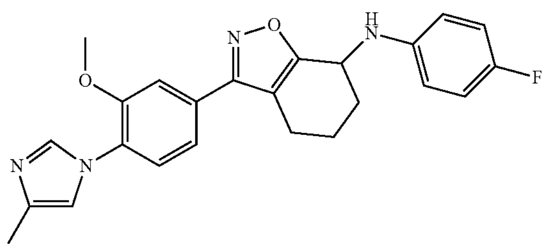 [SMILES: COc1cc(-c2noc3c2CCCC3Nc2ccc(F)cc2)ccc1-n1cnc(C)c1] | enantiomer 2 detailed procedure given | 419 | Method 1 | 402.6 | 37 |
| | racemic | 433 | Method 1 | 131.0 | Not Tested |
| | racemic | 447 | Method 1 | 319.0 | Not Tested |
| | racemic | 339 | Method 1 | 12176.9 | Not Tested |

TABLE-continued

| Structure | Comments | MS(M + H)+ | Method | Aβ42 IC50, nM | % CSF Aβ42 Reduction After 30 mg/kg Dosing |
|---|---|---|---|---|---|
| | racemic | 407 | Method 1 | 310.5 | Not Tested |
| | racemic | 407 | Method 1 | 464.1 | Not Tested |
| | racemic | 447 | Method 1 | 254.6 | Not Tested |
| 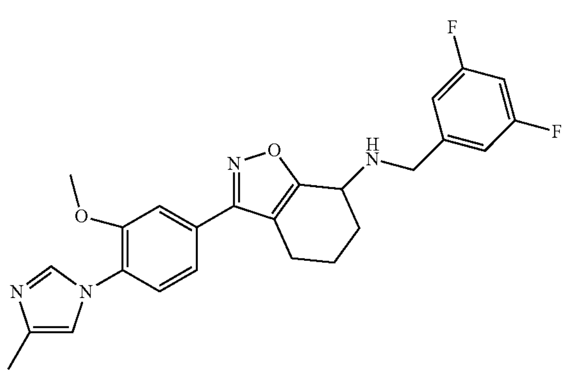 [SMILES: COc1cc(-c2noc3c2CCCC3NCc2cc(F)cc(F)c2)ccc1-n1cnc(C)c1] | enantiomer 1 | 451 | Method 1 | 644.5 | 7 |

TABLE-continued
| Structure | Comments | MS(M + H)+ | Method | Aβ42 IC50, nM | % CSF Aβ42 Reduction After 30 mg/kg Dosing |
|---|---|---|---|---|---|
| 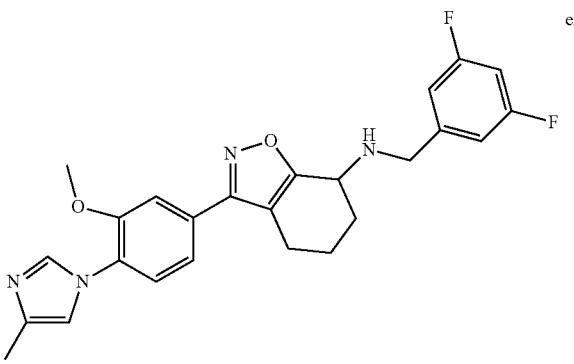 | enantiomer 2 | 451 | Method 1 | 29.4 | 20 |
| 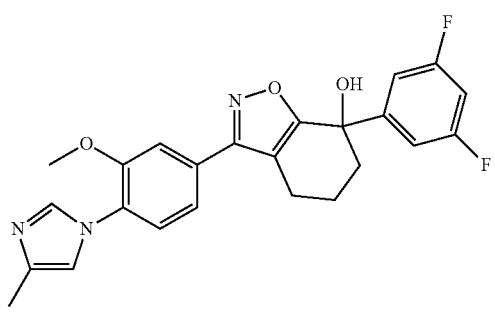 [SMILES: COc1cc(-c2noc3c2CCCC3(O)c2cc(F)cc(F)c2)ccc1-n1cnc(C)c1] | racemic detailed procedure given | 438 | Method 2 | 189.5 | 19 |
| 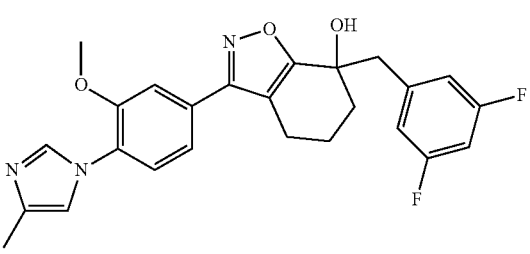 [SMILES: COc1cc(-c2noc3c2CCCC3(O)Cc2cc(F)cc(F)c2)ccc1-n1cnc(C)c1] | racemic | 452 | Method 2 | 150.3 | Not Tested |
| 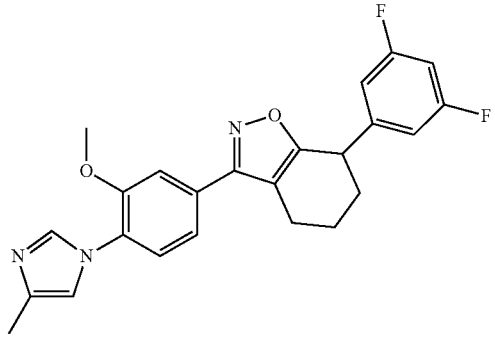 [SMILES: COc1cc(-c2noc3c2CCCC3c2cc(F)cc(F)c2)ccc1-n1cnc(C)c1] | racemic detailed procedure given | 422 | Method 3 | 112.6 | 0 |

| Structure | Comments | MS(M+H)+ | Method | Aβ42 IC50, nM | % CSF Aβ42 Reduction After 30 mg/kg Dosing |
|---|---|---|---|---|---|
| 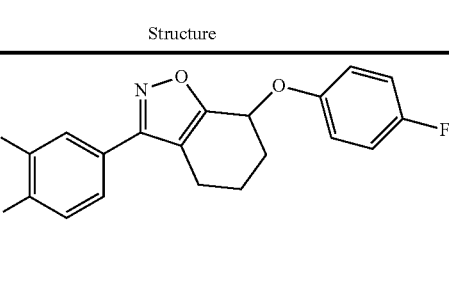 | racemic detailed procedure given | 420 | Method 4 | 295.1 | Not Tested |
| 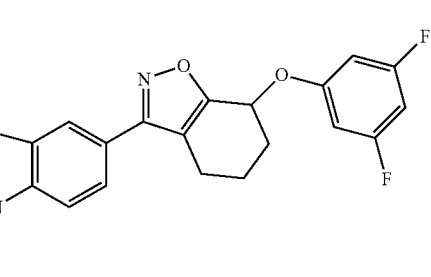 | racemic | 438 | Method 4 | 204.8 | Not Tested |
| 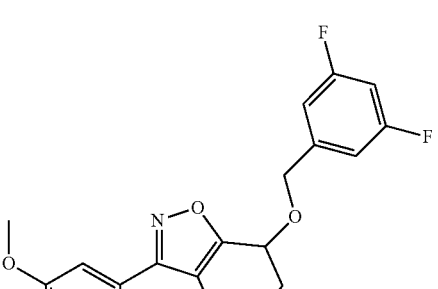 | racemic detailed procedure given | | Method 5 | 513.6 | Not Tested |

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

We claim:

1. A compound of the Formula (I)

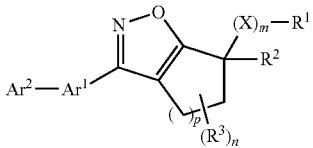

or a pharmaceutically acceptable salt thereof, wherein:

$R^1$ is 1) hydrogen, 2) (C1-C6)alkyl optionally substituted with 1 to 5 halogens or phenyl, wherein the phenyl is optionally substituted with 1 to 3 halogens, 3) phenyl optionally substituted with 1 to 3 (C1-C6)alkyls or 1 to 5 halogens, or 4) (C4-C6)cycloalkyl optionally substituted with 1 to 3 (C1-C6)alkyls or 1 to 5 halogens;

$R^2$ is 1) hydrogen, 2) (C1-C6)alkyl optionally substituted with 1 to 5 halogens or phenyl, wherein the phenyl is optionally substituted with 1 to 3 halogens, or 3) phenyl optionally substituted with 1 to 3 halogens;

$R^3$ is (C1-C6)alkyl, —OH or halogen;

X is —$NR^4$—, —O—, —S—, or —$SO_2$—;

$R^4$ is hydrogen or (C1-C3)alkyl;

p is 1 to 3;

m is 0 or 1;

n is 0 to 3; and

Ar²—Ar¹ is selected from the group consisting of

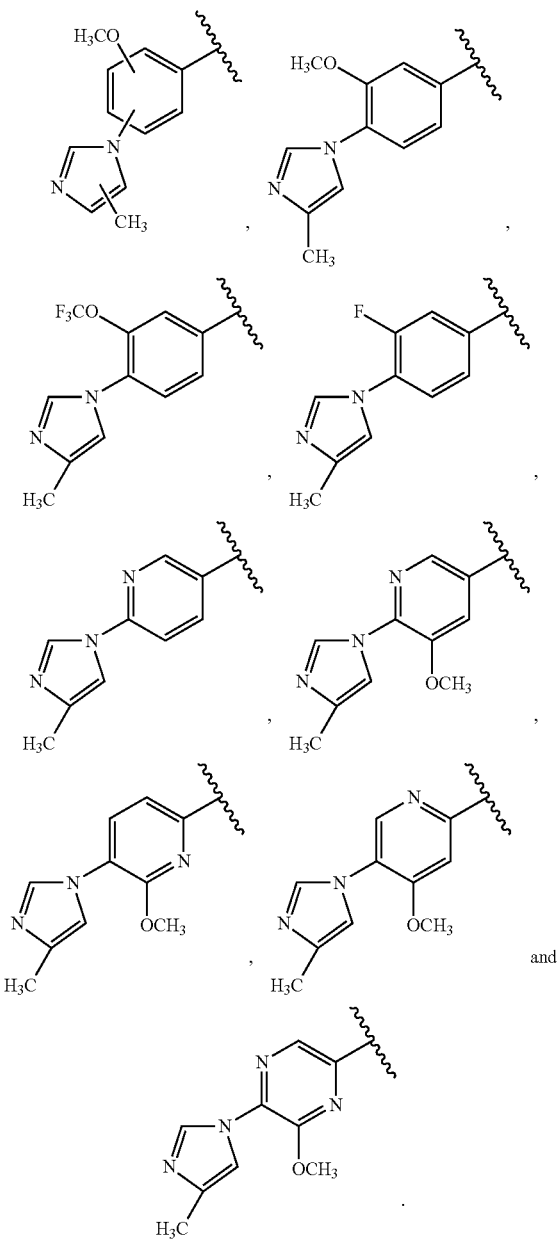

2. The compound of claim 1, wherein Ar²—Ar¹ is

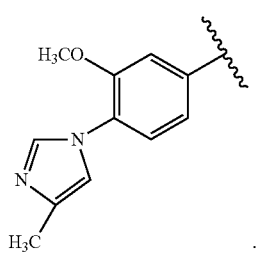

3. The compound of claim 1, wherein p is 2 and n is 0.
4. The compound of claim 1, wherein the halogen is fluoro.
5. The compound of claim 1, wherein X is —NR⁴—, m is 1, n is 0, and R¹ is (C1-C6)alkyl optionally substituted with 1 to 5 halogens or phenyl, wherein the phenyl is optionally substituted with 1 to 3 halogens.
6. The compound of claim 5, wherein R¹ is (C1-C6)alkyl substituted with phenyl, and wherein the phenyl is substituted with 1 or 2 halogens.
7. The compound of claim 6, wherein the halogen is fluoro.
8. The compound of claim 1, wherein X is —NR⁴—, m is 1, n is 0, and R¹ is phenyl optionally substituted with 1 to 3 (C1-C6)alkyls or 1 to 5 halogens.
9. The compound of claim 8, wherein R¹ is phenyl substituted with 1 or 2 halogens.
10. The compound of claim 9, wherein the halogen is fluoro.
11. The compound of claim 1, wherein X is —O—, m is 1, n is 0, and R¹ is 1) alkyl optionally substituted with 1 to 5 halogens or phenyl, wherein the phenyl is optionally substituted with 1 to 3 halogens or 2) phenyl optionally substituted with 1 to 3 (C1-C6)alkyls or 1 to 5 halogens.
12. The compound of claim 1, wherein X is —O—, m is 1, n is 0, R¹ is H, and R² is phenyl optionally substituted with 1 to 3 halogens.
13. The compound of claim 1, wherein X is —O—, m is 1, n is 0, R¹ is H, R² is (C1-C6)alkyl substituted with phenyl, wherein the phenyl is optionally substituted with 1 or 2 halogens.
14. The compound of claim 1, wherein X is —NR⁴—, m is 1, n is 0, and R¹ is (C4-C6)cycloalkyl optionally substituted with 1 to 3 (C1-C6)alkyls or 1 to 5 halogens.
15. A compound which is selected from the group consisting

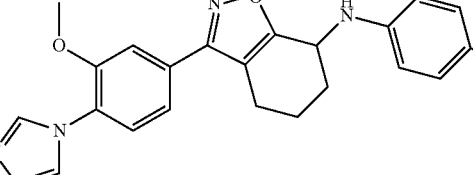

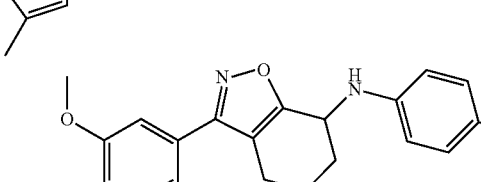

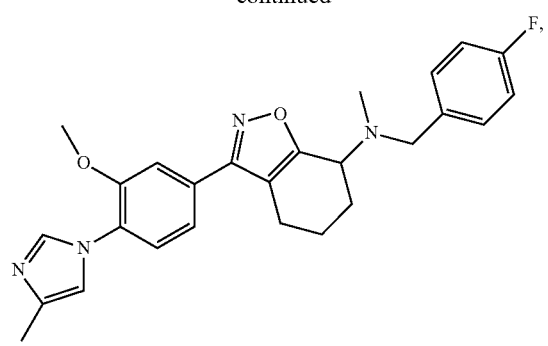
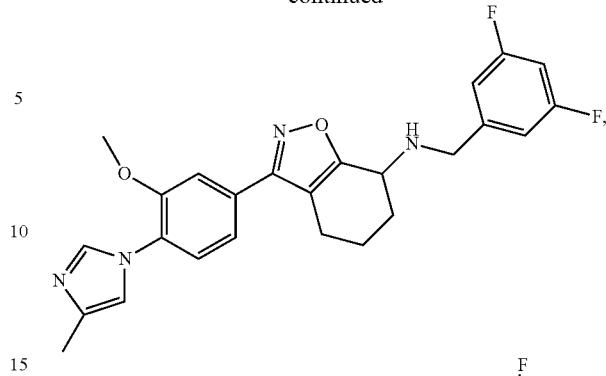
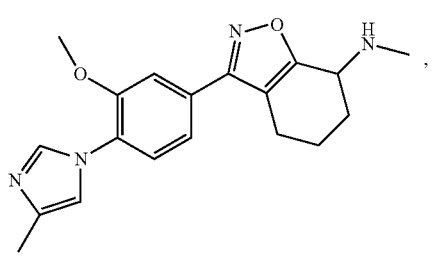
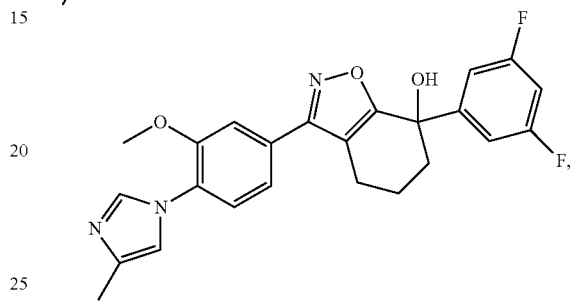
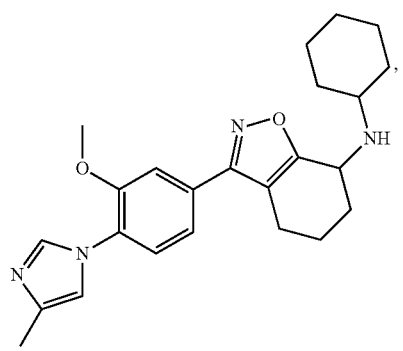
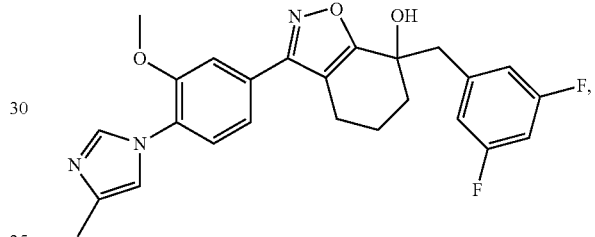
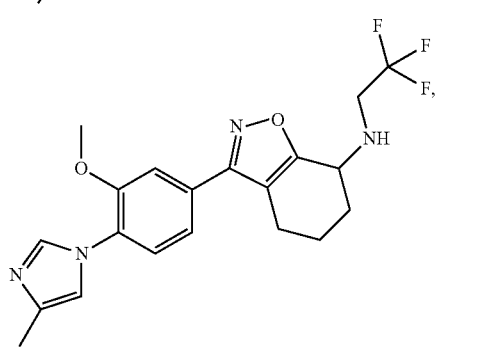
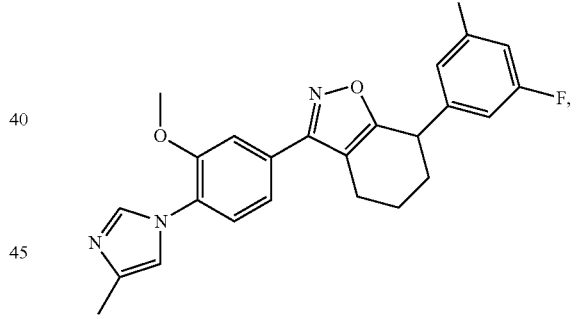
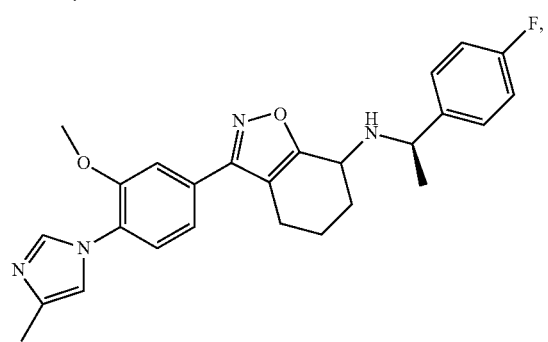

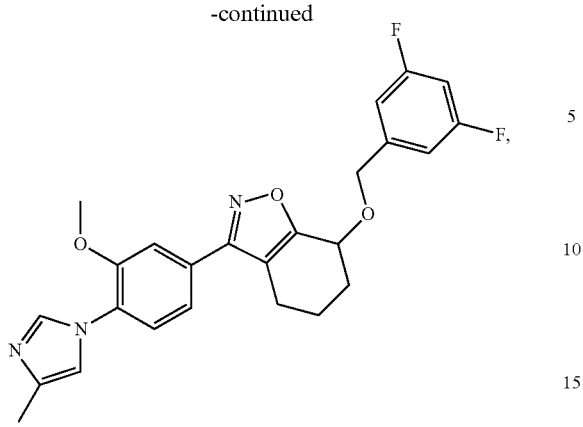

or a pharmaceutically acceptable salt thereof.

16. A pharmaceutical composition comprising the compound of claim 1 or a pharmaceutically acceptable salt thereof, and at least one pharmaceutically acceptable carrier.

17. A pharmaceutical composition comprising the compound of claim 15 or a pharmaceutically acceptable salt thereof, and at least one pharmaceutically acceptable carrier.

18. A method of treating Alzheimer's disease comprising administering to a patient in need thereof a therapeutically effective amount of at least one compound of claim 1 or a pharmaceutically acceptable salt thereof.

* * * * *